(12) United States Patent
Kubota et al.

(10) Patent No.: US 9,139,603 B2
(45) Date of Patent: Sep. 22, 2015

(54) [3-(2-NORBORNYL)-2-NORBORNYL]SILANE COMPOUND AND MAKING METHOD

(71) Applicant: SHIN-ETSU CHEMICAL CO., LTD., Tokyo (JP)

(72) Inventors: Yasufumi Kubota, Joetsu (JP); Tohru Kubota, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 58 days.

(21) Appl. No.: 14/062,475

(22) Filed: Oct. 24, 2013

(65) Prior Publication Data
US 2014/0121398 A1    May 1, 2014

(30) Foreign Application Priority Data
Oct. 25, 2012  (JP) ................. 2012-235818

(51) Int. Cl.
  *C07F 7/08* (2006.01)
  *C07F 7/18* (2006.01)
  *C07F 7/12* (2006.01)

(52) U.S. Cl.
  CPC ............... *C07F 7/1836* (2013.01); *C07F 7/12* (2013.01); *C07F 7/122* (2013.01); *C07F 7/184* (2013.01)

(58) Field of Classification Search
  USPC .......................... 556/441, 465, 481
  See application file for complete search history.

(56) References Cited

U.S. PATENT DOCUMENTS 4,921,976 A * 5/1990 Kabeta ............... 556/428

FOREIGN PATENT DOCUMENTS

JP    1-132591 A    5/1989

OTHER PUBLICATIONS

Petrov et al., "The Preparation of Organosilicon Derivatives of Bicyclo-(2,2,1)-Heptane", The institute of Organic Chemistry of the Academy of Sciences of the USSR, Zhurhal Obshchei Khimii, Apr. 1961, vol. 31, No. 4. pp. 1199-1208.

* cited by examiner

*Primary Examiner* — Sudhakar Katakam
*Assistant Examiner* — Pancham Bakshi
(74) *Attorney, Agent, or Firm* — Birch, Stewart, Kolasch & Birch, LLP

(57) ABSTRACT

A [3-(2-norbornyl)-2-norbornyl]silane compound having formula (1) is novel, wherein $R^1$ is a monovalent hydrocarbon radical, X is halogen or an organoxy $OR^2$, $R^2$ is a monovalent hydrocarbon radical, n is 1 or 2 when X is halogen, and n is 0, 1 or 2 when X is organoxy. It is a useful reactant for forming surface coatings on electronic parts.

(1)

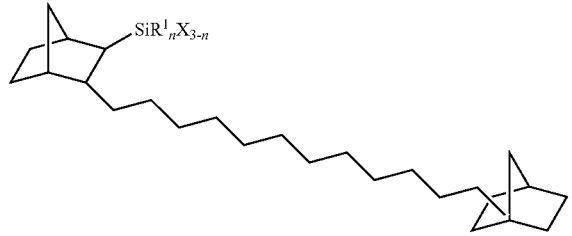

6 Claims, 8 Drawing Sheets

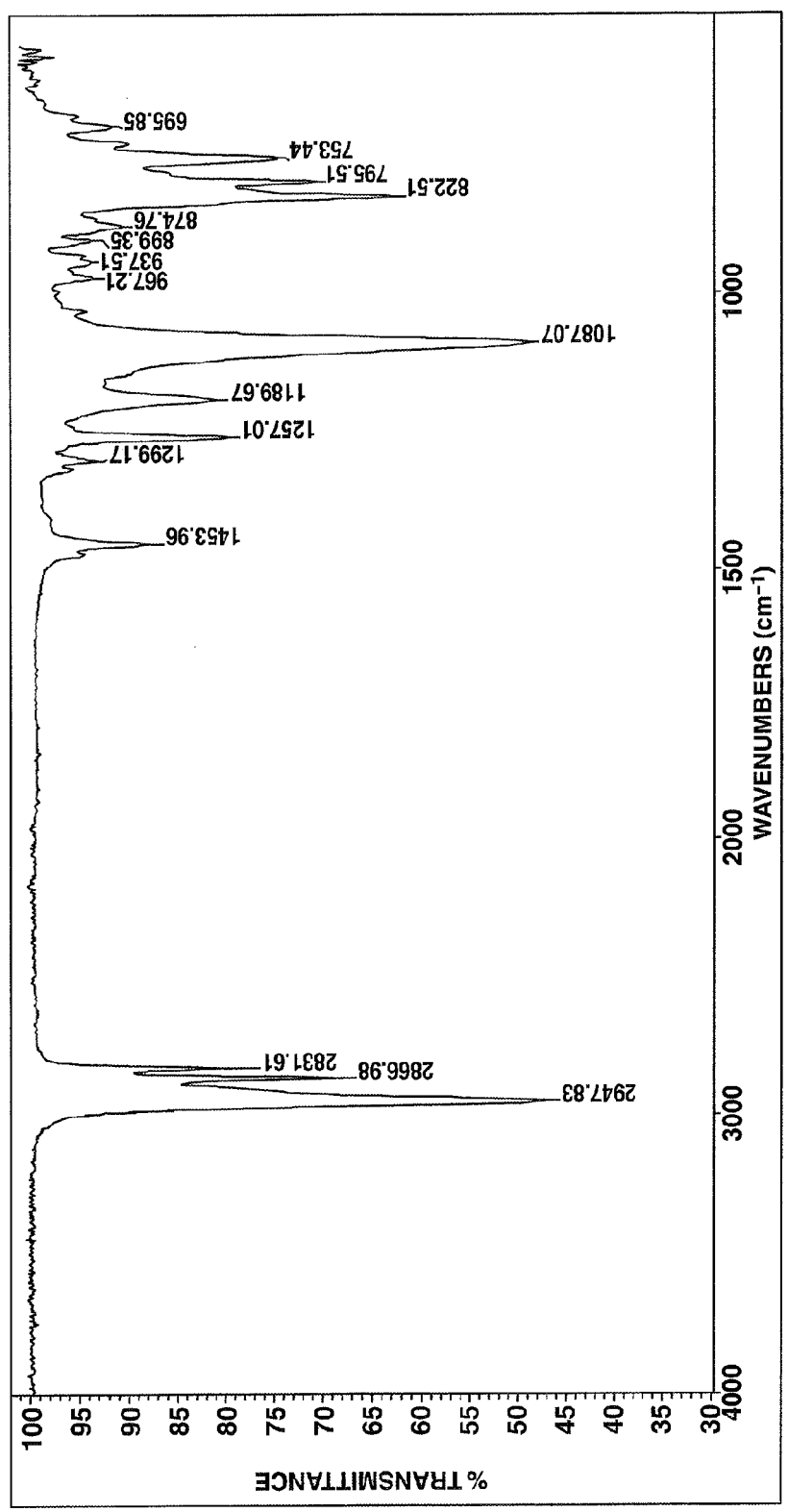

[3-(2-NORBORNYL)-2-NORBORNYL]SILANE COMPOUND AND MAKING METHOD

CROSS-REFERENCE TO RELATED APPLICATION

This non-provisional application claims priority under 35 U.S.C. §119(a) on Patent Application No. 2012-235818 filed in Japan on Oct. 25, 2012, the entire contents of which are hereby incorporated by reference.

TECHNICAL FIELD

This invention relates to a [3-(2-norbornyl)-2-norbornyl] silane compound and a method for preparing the same by reacting 2-norbornene with a hydrosilane compound in the presence of a catalyst composed of a phosphine-free palladium compound and a phosphite compound.

BACKGROUND ART

Silane compounds having a norbornyl radical are useful as reactants for various silicone compounds (for use in paint, adhesives, and high refractive index materials), coupling agents, coating composition ingredients, and organic synthesis intermediates. While norbornyl-containing compounds are known to have a high refractive index and thus used in high refractive index materials, they are still insufficient in refractive index. While a compound having a higher refractive index is desired, there is a need for a silane compound having a linkage of two norbornyl radicals.

For example, Patent Document 1 discloses a method for preparing a vinyl-containing [3-(2-norbornyl)-2-norbornyl] silane compound by reacting 5-vinyl-2-norbornene with a hydrosilane compound in the presence of metallic palladium or a palladium complex containing no phosphorus compound as a ligand.

It is known from Non-Patent Document 1 that a silane compound having a linkage of two unsubstituted norbornyl radicals, typically [3-(2-norbornyl)-2-norbornyl]trichlorosilane is formed as a by-product in hydrosilylation reaction between 2-norbornene and trichlorosilane in the presence of an isopropanol solution of chloroplatinic acid as a catalyst.

However, the vinyl-containing [3-(2-norbornyl)-2-norbornyl]silane compound is not suitable as a reactant for forming coatings on electronic parts. When the compound is subjected to hydrolysis and formulated in a silicone coating composition, the composition can be colored with time due to oxidation of vinyl in the molecule.

While a silicone oil as a high refractive index material ingredient is formed by co-hydrolysis of a silane compound having a linkage of two norbornyl radicals, for example, [3-(2-norbornyl)-2-norbornyl]trichlorosilane and another silane compound, the amount of the trichlorosilane (which is trifunctional) added must be limited in order that the resulting compound remain oily. There is thus a need for a difunctional silane compound having a linkage of two norbornyl radicals, for example, [3-(2-norbornyl)-2-norbornyl]organodichlorosilane which can be added in a higher proportion without depriving the product of oiliness. Also, for use as coupling agent after hydrolysis, a silane compound having a linkage of two norbornyl radicals, for example, [3-(2-norbornyl)-2-norbornyl]organoxysilane is desirable because no corrosive hydrogen chloride is formed as by-product.

Accordingly, it is desirable to have a difunctional silane compound having a linkage of two norbornyl radicals and free of an aliphatic unsaturated radical such as vinyl or an organoxysilane compound having a [3-(2-norbornyl)-2-norbornyl] radical. It is also desirable to have a method for preparing [3-(2-norbornyl)-2-norbornyl]trichlorosilane in high yields.

CITATION LIST

Patent Document 1: JP-A H01-132591

Non-patent Document 1: A. D. Petrov, et al., Zhurnal Obschchei Khimii (1961), 31, 1199-1208

DISCLOSURE OF INVENTION

An object of the invention is to provide a [3-(2-norbornyl)-2-norbornyl]organodichlorosilane and an organoxysilane compound having a [3-(2-norbornyl)-2-norbornyl] radical as a difunctional silane compound having a linkage of two norbornyl radicals. Another object is to provide a method for preparing a [3-(2-norbornyl)-2-norbornyl]silane compound in high yields through reaction of 2-norbornene with a hydrosilane compound in the presence of a catalyst composed of a phosphine-free palladium compound and a phosphite compound added thereto.

The inventors have found that a difunctional [3-(2-norbornyl)-2-norbornyl]organodichlorosilane and an organoxysilane compound having a [3-(2-norbornyl)-2-norbornyl] radical can be prepared using both a phosphine-free palladium compound and a phosphite compound as a catalyst, and that the catalyst ensures production of a [3-(2-norbornyl)-2-norbornyl]silane compound in high yields as compared with conventional catalysts.

In a first aspect, the invention provides a [3-(2-norbornyl)-2-norbornyl]silane compound having the general formula (1):

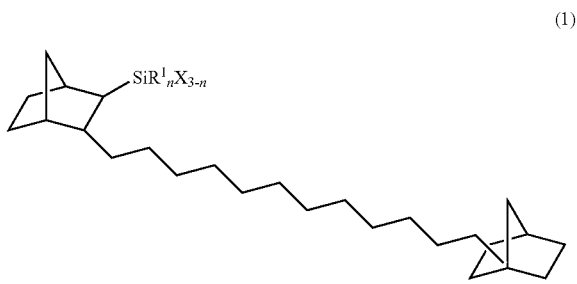

(1)

wherein $R^1$ is each independently a substituted or unsubstituted monovalent hydrocarbon radical of 1 to 10 carbon atoms, X is a halogen atom or an organoxy radical $OR^2$, $R^2$ is each independently a substituted or unsubstituted monovalent hydrocarbon radical of 1 to 10 carbon atoms, n is 1 or 2 when X is halogen, and n is 0, 1 or 2 when X is an organoxy radical.

In a second aspect, the invention provides a method for preparing a [3-(2-norbornyl)-2-norbornyl]halosilane compound having the general formula (3):

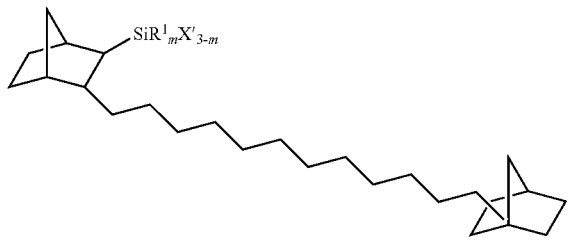

(3)

wherein R¹ is each independently a substituted or unsubstituted monovalent hydrocarbon radical of 1 to 10 carbon atoms, X' is a halogen atom, and m is 0, 1 or 2, the method comprising the step of reacting a hydrosilane compound having the general formula (2):

$HSiR^1_m X'_{3-m}$ (2)

wherein R', X' and m are defined as above, with 2-norbornene in the presence of a phosphine-free palladium compound and a phosphite compound.

In a preferred embodiment, the phosphite compound has the general formula (4):

$P(OR^3)(OR^4)(OR^5)$ (4)

wherein R³, R⁴ and R⁵ are each independently a substituted or unsubstituted monovalent hydrocarbon radical of 1 to 10 carbon atoms. Most typically, the palladium compound is palladium acetate. Also preferably, m is 1 or 2, and X' is chlorine.

In a third aspect, the invention provides a method for preparing a [3-(2-norbornyl)-2-norbornyl]organoxysilane compound, comprising the step of reacting a [3-(2-norbornyl)-2-norbornyl]halosilane compound resulting from the method of the second aspect with an alcohol having the formula: R'OH wherein R' is a substituted or unsubstituted monovalent hydrocarbon radical of 1 to 10 carbon atoms.

ADVANTAGEOUS EFFECTS OF INVENTION

According to the invention, [3-(2-norbornyl)-2-norbornyl]silane compounds can be prepared in high yields. They are useful as a reactant for forming surface coatings on electronic parts.

BRIEF DESCRIPTION OF DRAWINGS

FIGS. 7 and 8 show ¹H-NMR and IR spectra of [3-(2-norbornyl)-2-norbornyl]methyldimethoxysilane synthesized in Example 4, respectively.

DESCRIPTION OF EMBODIMENTS

Figure 1:
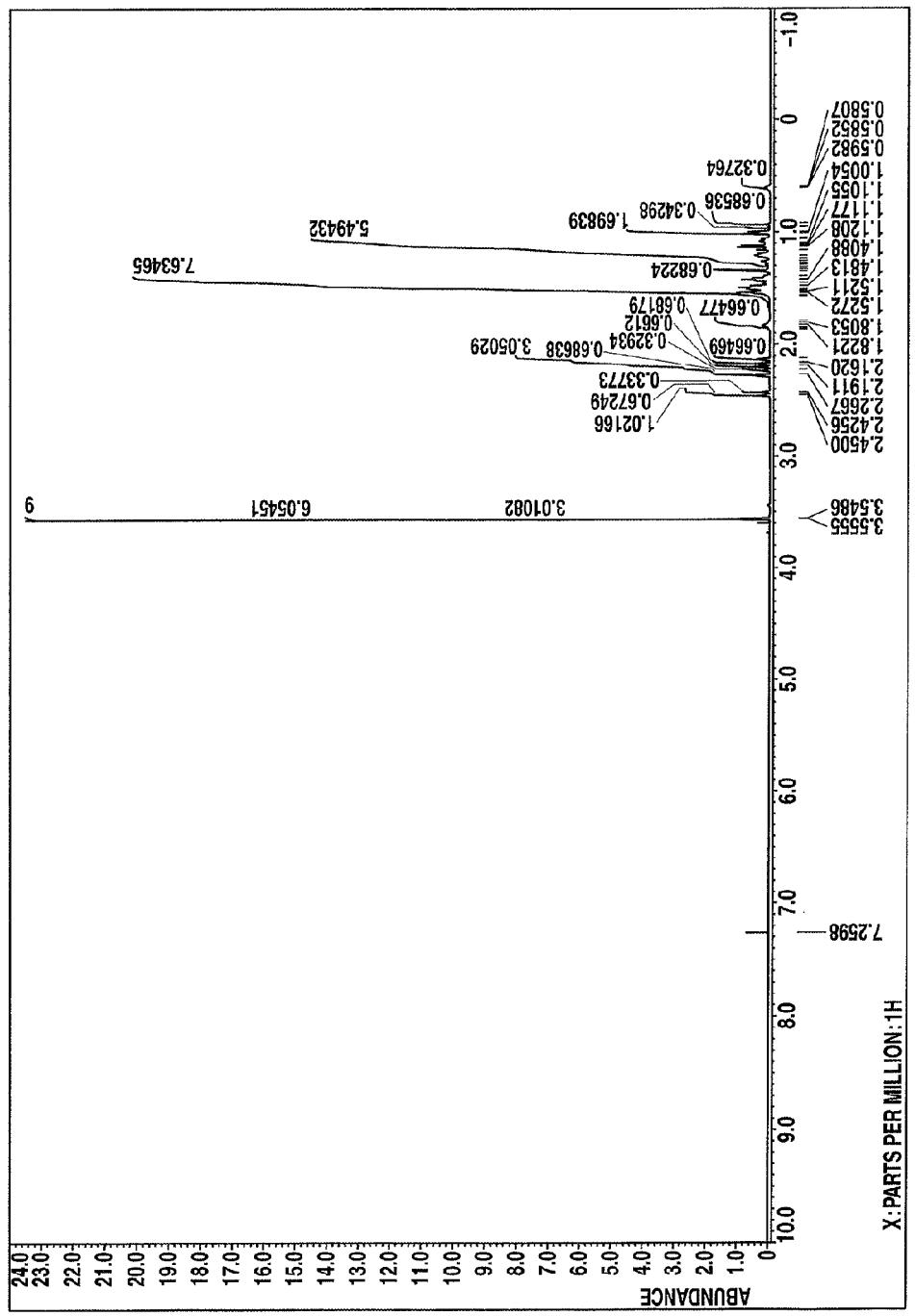
FIGS. 1 and 2 show ¹H-NMR and IR spectra of [3-(2-norbornyl)-2-norbornyl]trimethoxysilane synthesized in Example 1, respectively.

The invention provides a [3-(2-norbornyl)-2-norbornyl]silane compound having the general formula (1).

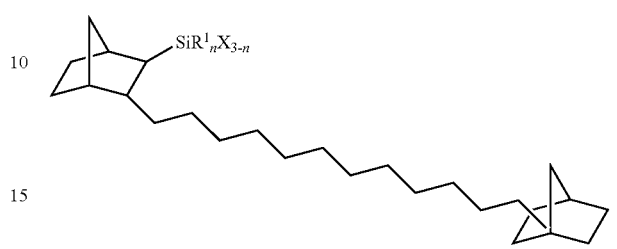

(1)

Herein R¹ is each independently a substituted or unsubstituted monovalent hydrocarbon radical of 1 to 10 carbon atoms. X is a halogen atom or an organoxy radical OR², wherein R² is each independently a substituted or unsubstituted monovalent hydrocarbon radical of 1 to 10 carbon atoms. The subscript n is 1 or 2 when X is halogen, and n is 0, 1 or 2 when X is organoxy.

R¹ is a substituted or unsubstituted monovalent hydrocarbon radical of 1 to 10 carbon atoms, examples of which include straight, branched or cyclic alkyl, alkenyl, aryl, and aralkyl radicals. Examples include methyl, ethyl, propyl, isopropyl, butyl, isobutyl, tert-butyl, pentyl, cyclopentyl, hexyl, thexyl, cyclohexyl, heptyl, octyl, 2-ethylhexyl, decyl, vinyl, propenyl, phenyl, tolyl and benzyl and, substituted forms of the foregoing in which some or all hydrogen atoms are substituted. Suitable substituents include alkoxy radicals such as methoxy, ethoxy and (iso)propoxy, halogen atoms such as fluorine, chlorine, and iodine, cyano radicals, aromatic hydrocarbon radicals, alkylsilyl radicals, and combinations thereof.

X is a halogen atom or an organoxy radical OR². Exemplary halogens include chlorine, fluorine and iodine. Of these, chlorine is preferred because a hydrosilane compound as the starting reactant is readily available. The substituted or unsubstituted monovalent hydrocarbon radical of 1 to 10 carbon atoms represented by R² is as exemplified above for R¹.

Examples of the [3-(2-norbornyl)-2-norbornyl]silane compound having formula (1) include
[3-(2-norbornyl)-2-norbornyl]methyldichlorosilane,
[3-(2-norbornyl)-2-norbornyl]dimethylchlorosilane,
[3-(2-norbornyl)-2-norbornyl]ethyldichlorosilane,
[3-(2-norbornyl)-2-norbornyl]diethylchlorosilane,
[3-(2-norbornyl)-2-norbornyl]propyldichlorosilane,
[3-(2-norbornyl)-2-norbornyl]dipropylchlorosilane,
[3-(2-norbornyl)-2-norbornyl]trimethoxysilane,
[3-(2-norbornyl)-2-norbornyl]triethoxysilane,
[3-(2-norbornyl)-2-norbornyl]methyldimethoxysilane,
[3-(2-norbornyl)-2-norbornyl]methyldiethoxysilane,
[3-(2-norbornyl)-2-norbornyl]ethyldimethoxysilane,
[3-(2-norbornyl)-2-norbornyl]ethyldiethoxysilane,
[3-(2-norbornyl)-2-norbornyl]propyldimethoxysilane,
[3-(2-norbornyl)-2-norbornyl]propyldiethoxysilane,
[3-(2-norbornyl)-2-norbornyl]dimethylmethoxysilane,
[3-(2-norbornyl)-2-norbornyl]dimethylethoxysilane,
[3-(2-norbornyl)-2-norbornyl]diethylmethoxysilane,
[3-(2-norbornyl)-2-norbornyl]diethylethoxysilane,
[3-(2-norbornyl)-2-norbornyl]dipropylmethoxysilane, and
[3-(2-norbornyl)-2-norbornyl]dipropylethoxysilane.

According to the method of the invention, a [3-(2-norbornyl)-2-norbornyl]halosilane compound having the general formula (3) is prepared by reacting a hydrosilane compound having the general formula (2) with 2-norbornene in the presence of a catalyst composed of a phosphine-free palladium compound and a phosphite compound added thereto.

$$HSiR^1{}_mX'_{3-m} \quad (2)$$

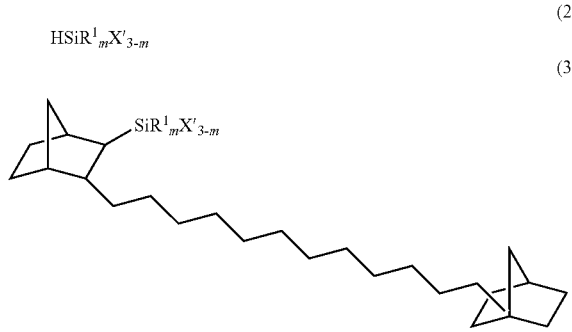

(3)

Herein $R^1$ is defined as above, $X'$ is a halogen atom, and m is 0, 1 or 2. Exemplary groups of $R^1$ in formula (2) are the same as exemplified above in conjunction with formula (1).

Examples of the hydrosilane compound having formula (2) include trichlorosilane, methyldichlorosilane, ethyldichlorosilane, propyldichlorosilane, dimethylchlorosilane, diethylchlorosilane, and dipropylchlorosilane.

Examples of the [3-(2-norbornyl)-2-norbornyl]halosilane compound having formula (3) include
[3-(2-norbornyl)-2-norbornyl]trichlorosilane,
[3-(2-norbornyl)-2-norbornyl]methyldichlorosilane,
[3-(2-norbornyl)-2-norbornyl]dimethylchlorosilane,
[3-(2-norbornyl)-2-norbornyl]ethyldichlorosilane,
[3-(2-norbornyl)-2-norbornyl]diethylchlorosilane,
[3-(2-norbornyl)-2-norbornyl]propyldichlorosilane, and
[3-(2-norbornyl)-2-norbornyl]dipropylchlorosilane.

In the reaction of 2-norbornene with a hydrosilane compound, they may be combined in any desired ratio. It is preferred from the aspects of reactivity and productivity that 0.2 to 1.0 mole, more preferably 0.25 to 0.7 mole and even more preferably 0.4 to 0.6 mole of hydrosilane compound be used per mole of 2-norbornene.

Examples of the phosphine-free palladium compound include palladium chloride, dichloro(1,5-cyclooctadiene)-palladium, and palladium acetate. Of these, palladium acetate is preferred from the aspects of reactivity and catalyst stability.

The amount of the phosphine-free palladium compound used is not particularly limited. From the aspects of reactivity and productivity, it is preferably 0.000001 to 0.01 mole, more preferably 0.000005 to 0.005 mole, and even more preferably 0.00001 to 0.001 mole per mole of 2-norbornene. Less than 0.000001 mole of the phosphine-free palladium compound may fail to exert a sufficient catalytic effect. If the amount of the phosphine-free palladium compound exceeds 0.01 mole, a reaction promoting effect commensurate with that catalyst amount may not be obtained.

The phosphite compound preferably has the general formula (4):

wherein $R^3$, $R^4$ and $R^5$ are each independently a substituted or unsubstituted monovalent hydrocarbon radical of 1 to 10 carbon atoms.

In formula (4), $R^3$, $R^4$ and $R^5$ are each independently selected from substituted or unsubstituted monovalent hydrocarbon radicals, which include straight, branched or cyclic aliphatic monovalent hydrocarbon radicals such as straight, branched or cyclic alkyl, aryl, and aralkyl radicals. Examples include methyl, ethyl, propyl, butyl, pentyl, hexyl, phenyl, benzyl, isopropyl, isobutyl, sec-butyl, tert-butyl, neopentyl, 2-ethylhexyl, cyclopentyl, and cyclohexyl.

Examples of the phosphite compound having formula (4) include trimethyl phosphite, triethyl phosphite, tripropyl phosphite, tributyl phosphite, triisobutyl phosphite, tripentyl phosphite, trihexyl phosphite, tri(2-ethylhexyl) phosphite, triisopropyl phosphite, tri-sec-butyl phosphite, tri-tert-butyl phosphite, tricyclopentyl phosphite, tricyclohexyl phosphite, triphenyl phosphite, tribenzyl phosphite, and tris(trimethylsilyl)phosphite.

Although the amount of the phosphite compound used is not particularly limited, it is preferred for reactivity and selectivity that the phosphite compound be used in an amount of 1.0 to 10.0 moles, more preferably 1.5 to 8.0 moles, and even more preferably 3.0 to 6.0 moles per mole of palladium in the phosphine-free palladium compound. If the amount of the phosphite compound used is less than 1.0 mole, the selectivity of reaction may be reduced or the reaction may not take place. If the amount of the phosphite compound used exceeds 10.0 moles, the reactivity may be reduced.

Although the reaction may take place in a solventless system, a solvent may be used. Examples of the solvent used include hydrocarbon solvents such as pentane, hexane, cyclohexane, heptane, octane, isooctane, benzene, toluene, xylene and mesitylene, ether solvents such as diethyl ether, tetrahydrofuran and dioxane, aprotic polar solvents such as acetonitrile, and chlorinated hydrocarbon solvents such as dichloromethane and chloroform. These solvents may be used alone or in admixture of two or more. Since 2-norbornene is a compound having a melting point of 44-46° C. which is solid at room temperature, it may be used as a solution in the foregoing solvent for ease of handling.

The relevant reaction may be performed by adding the hydrosilane compound having formula (2) to 2-norbornene and a catalyst which is obtained by adding a phosphite compound to a phosphine-free palladium compound. Alternatively, 2-norbornene may be added to the hydrosilane compound having formula (2) and a catalyst which is obtained by adding a phosphite compound to a phosphine-free palladium compound. In the case of post-addition of 2-norbornene, it is preferably dissolved in a solvent prior to its addition.

Although reaction of 2-norbornene with the hydrosilane compound having formula (2) may be initiated immediately after a phosphine-free palladium compound and a phosphite compound having formula (4) are added to 2-norbornene or the hydrosilane to form a mixture, it is desired that the mixture be stirred for 1 to 10 hours, preferably 2 to 4 hours at elevated temperature prior to the reaction. Specifically, the preferred reaction procedure involves adding the phosphine-free palladium compound and the phosphite compound to a solution of 2-norbornene in toluene or the like, stirring the mixture at 80 to 90° C. for 1 to 10 hours, more preferably 2 to 4 hours, thereafter adding the hydrosilane compound having formula (2) to the mixture, and allowing reaction to run. Stirring of the mixture at elevated temperature prior to addition of the hydrosilane compound is effective for improving the production ratio of the desired [3-(2-norbornyl)-2-norbornyl]halosilane having formula (3), as determined from peak areas of gas chromatography.

The reaction temperature is typically in a range of 0° C. to 200° C., preferably 10° C. to 120° C. under atmospheric or applied pressure, though not limited thereto. The reaction time is typically 1 to 100 hours, preferably 2 to 20 hours. Although the reaction atmosphere is not particularly limited, an inert gas atmosphere such as nitrogen, argon or helium is preferred for safety.

Also the compound having formula (1) in which X is an organoxy radical $OR^2$ can be prepared by reacting a corresponding [3-(2-norbornyl)-2-norbornyl]halosilane compound having formula (3) with an alcohol having the formula: $R^2OH$ wherein $R^2$ is as defined above.

Examples of the alcohol: $R^2OH$ wherein $R^2$ is as defined above include methanol, ethanol, n-propanol, isopropanol, and n-butanol. The alcohol is preferably used in an amount of 0.8 to 2.0 moles, more preferably 1.0 to 1.3 moles per mole of halogen.

The reaction with alcohol may be performed while removing hydrogen halide by-product from the reaction system. If the reaction is performed in the presence of a base, the reaction product of hydrogen halide by-product with the base may be removed. In the former reaction mode with removal of hydrogen halide, there is a possibility that hydrogen halide can react, before removal, with unreacted alcohol to form by-products, an alkyl halide and water, and the resulting water can react with a halosilane or a produced alkoxysilane from the halosilane to form a siloxane by-product, leading to low yields. For this reason, the latter reaction mode using a base is preferred.

Examples of the base used herein include triethylamine, tributylamine, trioctylamine, and pyridine. The base is preferably used in an amount of 0.8 to 2.0 moles, more preferably 1.0 to 1.3 moles per mole of halogen.

In the reaction mode using the base, since the base forms a hydrochloride salt as by-product, the reaction is preferably performed in a solvent. Examples of the solvent used herein include hydrocarbon solvents such as pentane, hexane, cyclohexane, heptane, octane, isooctane, benzene, toluene, xylene, and mesitylene.

The reaction temperature is preferably in a range of 0° C. to 150° C., more preferably 10° C. to 100° C. under atmospheric or applied pressure, though not limited thereto. The reaction time is typically 0.5 to 100 hours, preferably 1 to 20 hours. Although the reaction atmosphere is not particularly limited, an inert gas atmosphere such as nitrogen, argon or helium is preferred for safety. The reaction is preferably carried out by adding the alcohol to a mixture of the compound of formula (3), the solvent and the base.

EXAMPLE

Examples of the invention are given below by way of illustration and not by way of limitation.

Example 1

Preparation of [3-(2-norbornyl)-2-norbornyl]trimethoxysilane

A 1000-ml four-neck glass flask equipped with a reflux condenser, thermometer and stirrer was purged with nitrogen and charged with 94.2 g (1.0 mole) of 2-norbornene in 31.4 g of toluene, and 22.5 mg (0.0001 mole) of palladium acetate. The contents were stirred for dissolution, after which 104.2 mg (0.0005 mole) of triisopropyl phosphite was added. The solution was stirred for 3 hours while keeping the internal temperature at 85° C. to 95° C. Then, 81.3 g (0.6 mole) of trichlorosilane was added dropwise over 6 hours, followed by ripening at the temperature for 2 hours. To the resulting reaction solution, 42.2 g (1.32 moles) of methanol was added dropwise over 2 hours while keeping the internal temperature at 55° C. to 65° C. The solution was ripened for 1 hour. Further, 150 ml of toluene and 72.9 g (0.72 mole) of triethylamine were added and then 21.1 g (0.66 mole) of methanol was added dropwise over 1 hour. The solution was ripened for 1 hour. The hydrochloride salt formed was removed by filtration. On vacuum distillation, [3-(2-norbornyl)-2-norbornyl]trimethoxysilane was collected as a fraction at a boiling point of 123-124° C./0.4 kPa. Amount 128.9 g (0.415 mole), yield 83.0%.

Figure 2:
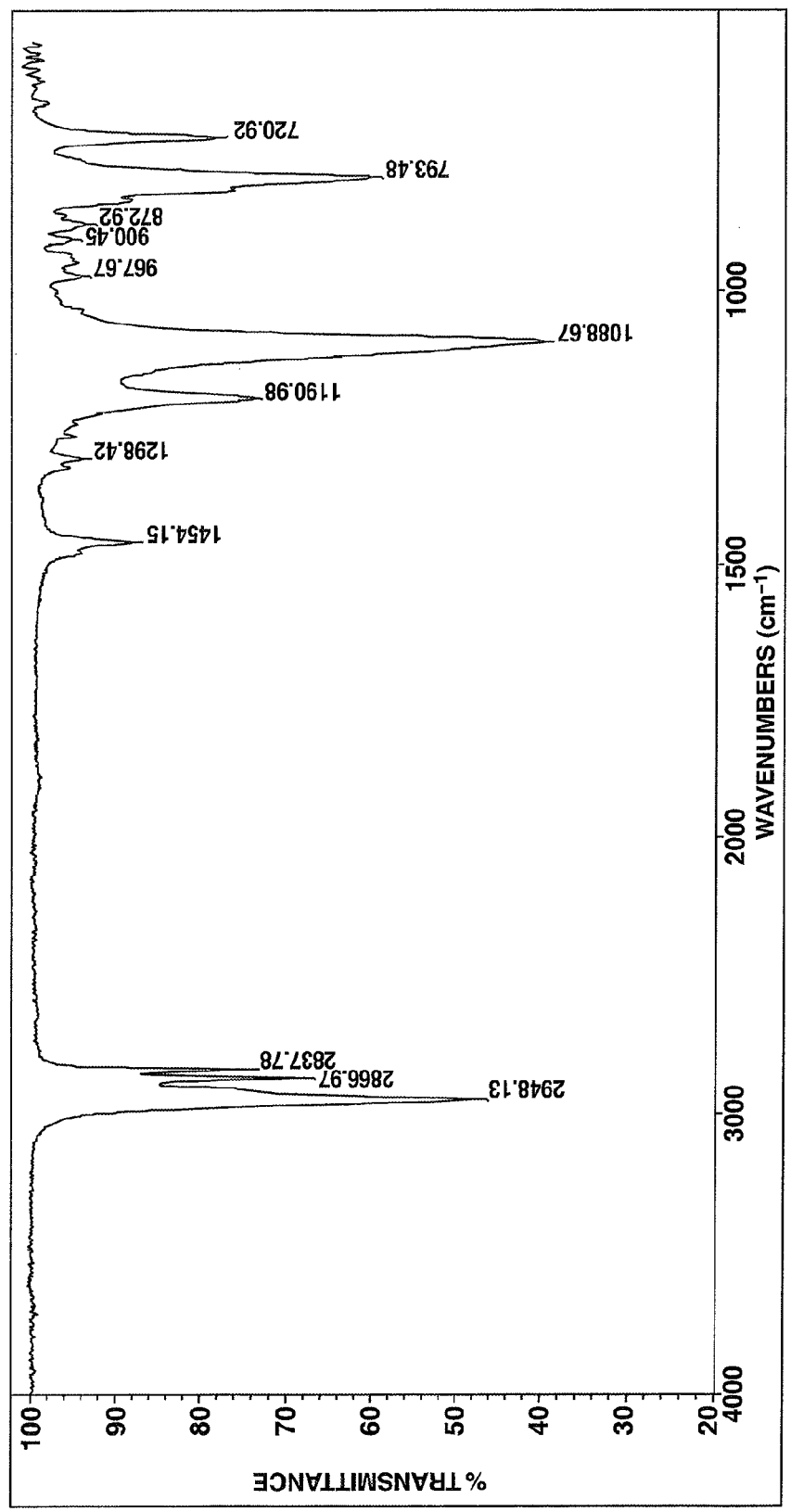

This fraction was analyzed by mass, $^1$H-NMR and IR spectroscopy, with the results shown below.
Mass Spectrum
m/z 310, 278, 215, 183, 121
$^1$H-NMR spectrum (deuterated chloroform): FIG. 1
IR Spectrum: FIG. 2
From these results, the compound was identified to be [3-(2-norbornyl)-2-norbornyl]trimethoxysilane.

Example 2

Preparation of [3-(2-norbornyl)-2-norbornyl]triethoxysilane

A [3-(2-norbornyl)-2-norbornyl]trichlorosilane reaction solution was obtained as in Example 1. To the reaction solution, 60.7 g (1.32 moles) of ethanol was added dropwise over 2 hours while keeping the internal temperature at 55° C. to 65° C. The solution was ripened for 1 hour. Further, 150 ml of toluene and 72.9 g (0.72 mole) of triethylamine were added and then 30.4 g (0.66 mole) of ethanol was added dropwise over 1 hour, followed by one hour of ripening. The hydrochloride salt formed was removed by filtration. On vacuum distillation, [3-(2-norbornyl)-2-norbornyl]triethoxysilane was collected as a fraction at a boiling point of 135-126° C./0.4 kPa. Amount 140.2 g (0.398 mole), yield 79.6%.

Figure 3:
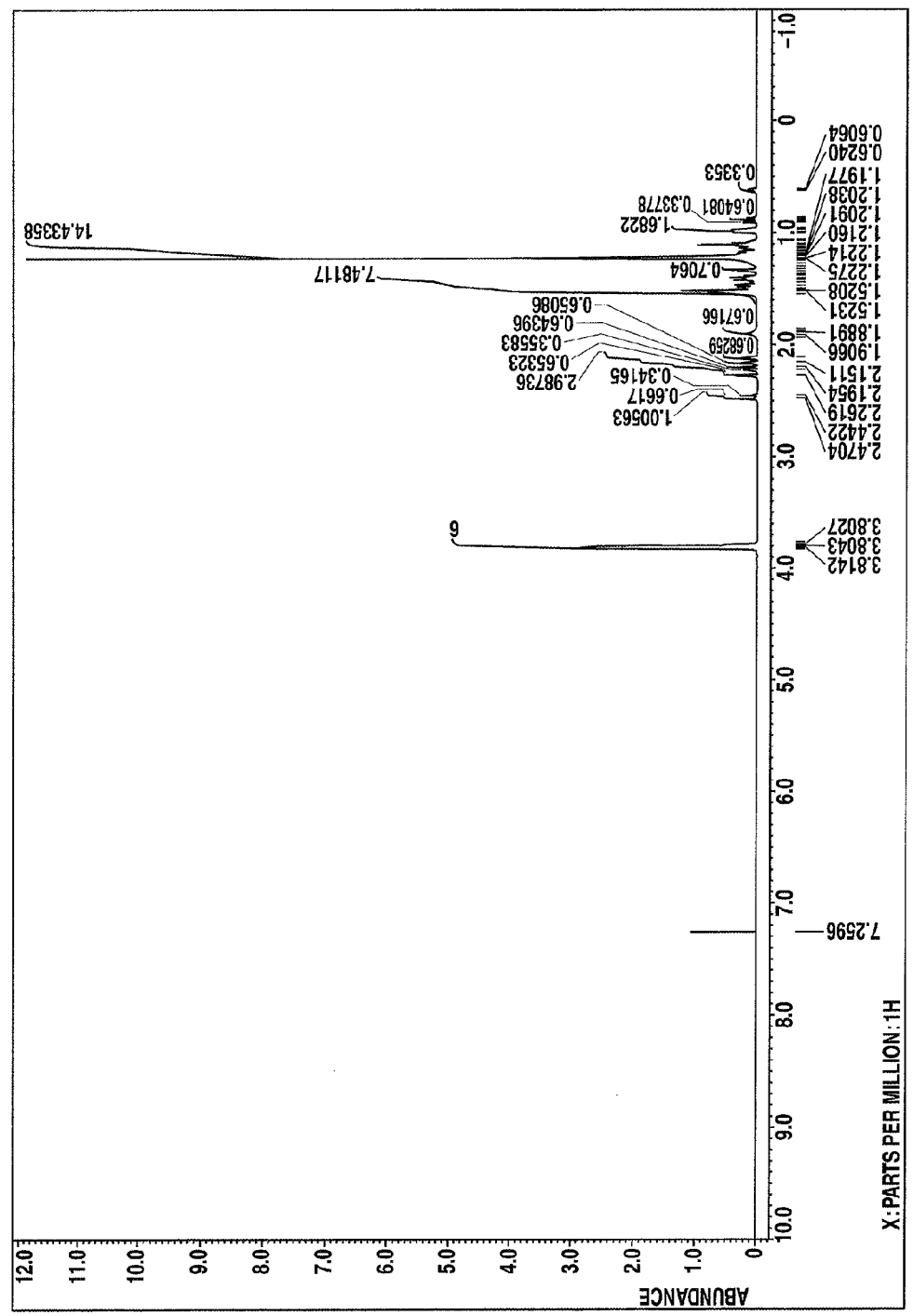
FIGS. 3 and 4 show ¹H-NMR and IR spectra of [3-(2-norbornyl)-2-norbornyl]triethoxysilane synthesized in Example 2, respectively.
Figure 4:
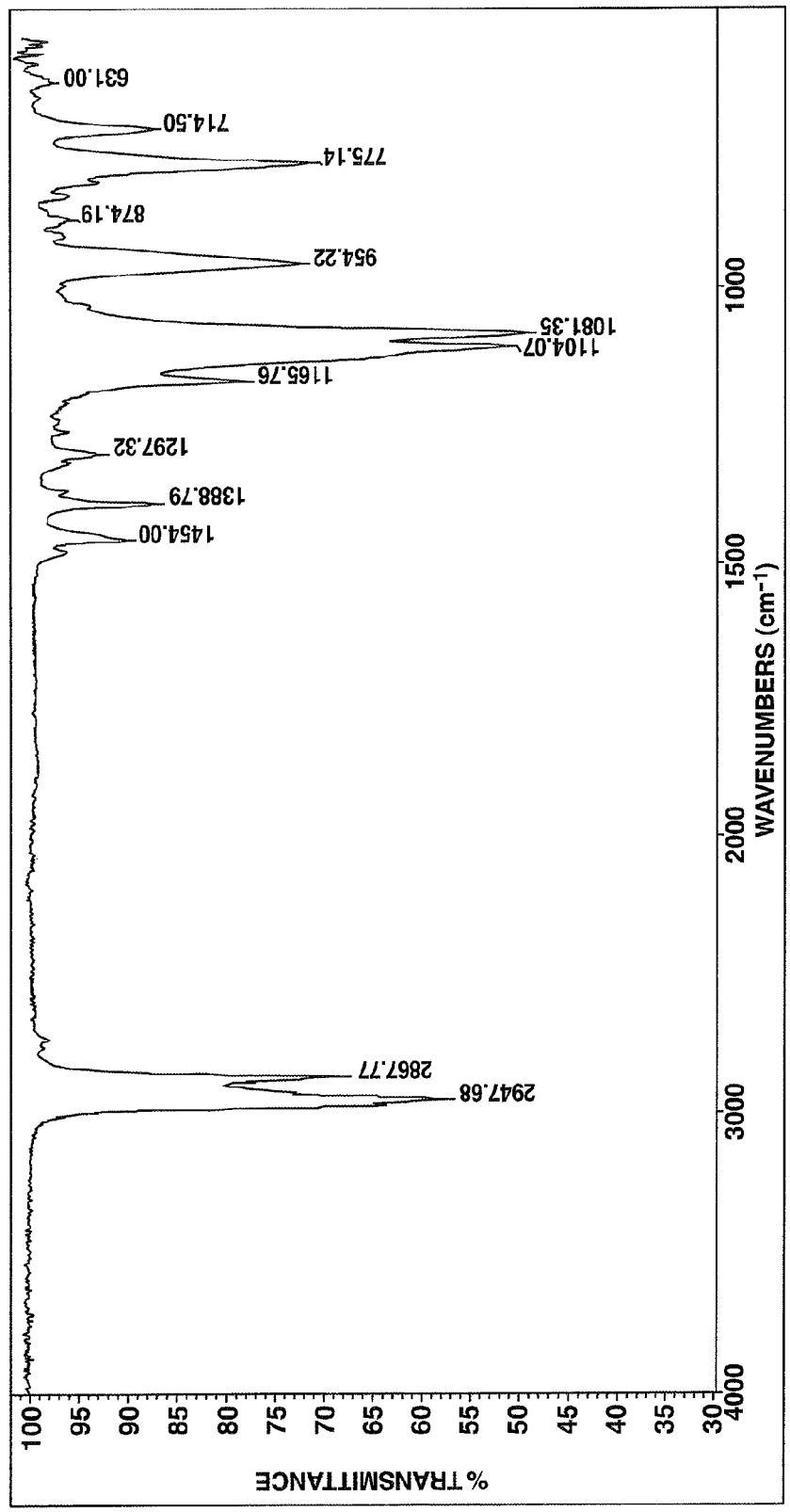

This fraction was analyzed by mass, $^1$H-NMR and IR spectroscopy.
Mass Spectrum
m/z 352, 324, 306, 257, 163
$^1$H-NMR spectrum (deuterated chloroform): FIG. 3
IR Spectrum: FIG. 4
From these results, the compound was identified to be [3-(2-norbornyl)-2-norbornyl]triethoxysilane.

Example 3

Preparation of [3-(2-norbornyl)-2-norbornyl]methyldichlorosilane

A 300-ml four-neck glass flask equipped with a reflux condenser, thermometer and stirrer was purged with nitrogen and charged with 94.2 g (1.0 mole) of 2-norbornene in 31.4 g of toluene, and 22.5 mg (0.0001 mole) of palladium acetate. The contents were stirred for dissolution, after which 104.2 mg (0.0005 mole) of triisopropyl phosphite was added. The solution was stirred for 3 hours while keeping the internal temperature at 85° C. to 95° C. Then 57.5 g (0.5 mole) of methyldichlorosilane was added dropwise over 12 hours while 11.2 mg of palladium acetate was added twice in the course. The solution was ripened at the same temperature for 10 hours.

On analysis of the resulting reaction solution by gas chromatography, the product ratio determined from peak areas of the desired [3-(2-norbornyl)-2-norbornyl]methyldichlorosilane:2-methyldichlorosilylnorbornane was 75.5:24.5. The reaction solution was distilled in vacuum, collecting [3-(2-norbornyl)-2-norbornyl]methyldichlorosilane as a fraction at a boiling point of 144-145° C./0.5 kPa. Amount 80.3 g (0.265 mole), yield 53.0%.

This fraction was analyzed by mass, $^1$H-NMR and IR spectroscopy.

Figure 5:
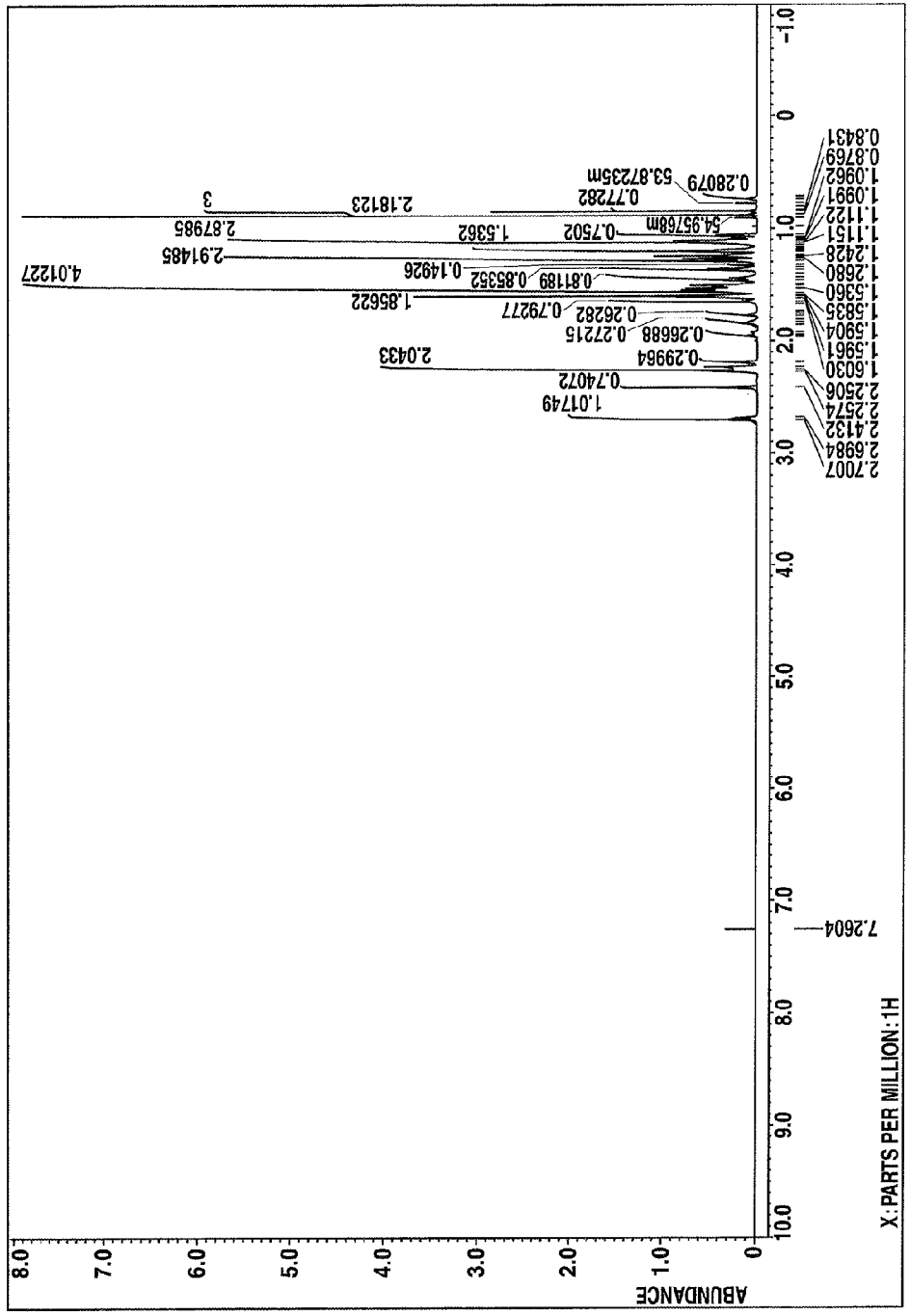
FIGS. 5 and 6 show ¹H-NMR and IR spectra of [3-(2-norbornyl)-2-norbornyl]methyldichlorosilane synthesized in Example 3, respectively.
Figure 6:
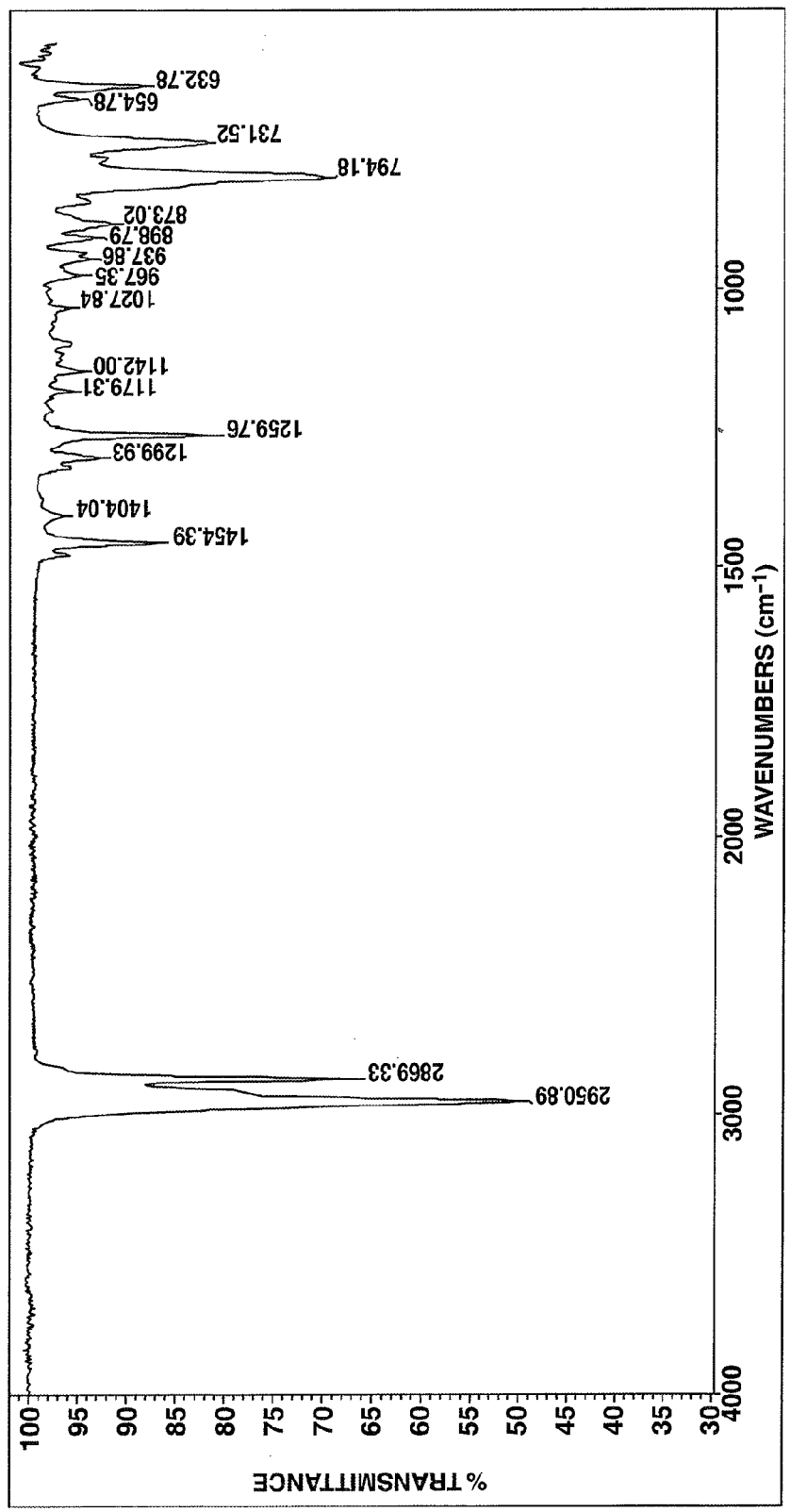

Mass Spectrum
m/z 302, 277, 261, 207, 189, 113, 95, 87
$^1$H-NMR spectrum (deuterated chloroform): FIG. 5
IR Spectrum: FIG. 6

From these results, the compound was identified to be [3-(2-norbornyl)-2-norbornyl]methyldichlorosilane.

Example 4

Preparation of
[3-(2-norbornyl)-2-norbornyl]methyldimethoxysilane

A 500-ml four-neck glass flask equipped with a reflux condenser, thermometer and stirrer was purged with nitrogen and charged with 94.2 g (1.0 mole) of 2-norbornene in 31.4 g of toluene, and 22.5 mg (0.0001 mole) of palladium acetate. The contents were stirred for dissolution, after which 104.2 mg (0.0005 mole) of triisopropyl phosphite was added. The solution was stirred for 3 hours while keeping the internal temperature at 85° C. to 95° C. Then, 57.5 g (0.5 mole) of methyldichlorosilane was added dropwise over 12 hours while 11.2 mg of palladium acetate was added twice in the course. The solution was ripened at the same temperature for 10 hours. To the resulting reaction solution, 17.6 g (0.55 mole) of methanol was added dropwise over 1 hour while keeping the internal temperature at 55° C. to 65° C. The solution was ripened for 1 hour. Further, 150 mL of toluene and 72.9 g (0.72 mole) of triethylamine were added and then 17.6 g (0.55 mole) of methanol was added dropwise over 1 hour, followed by one hour of ripening. The hydrochloride salt formed was removed by filtration. On vacuum distillation, [3-(2-norbornyl)-2-norbornyl]methyldimethoxysilane was collected as a fraction at a boiling point of 118-119° C./0.3 kPa. Amount 69.9 g (0.237 mole), yield 47.5%.

This fraction was analyzed by mass, $^1$H-NMR and IR spectroscopy.

Figure 7:
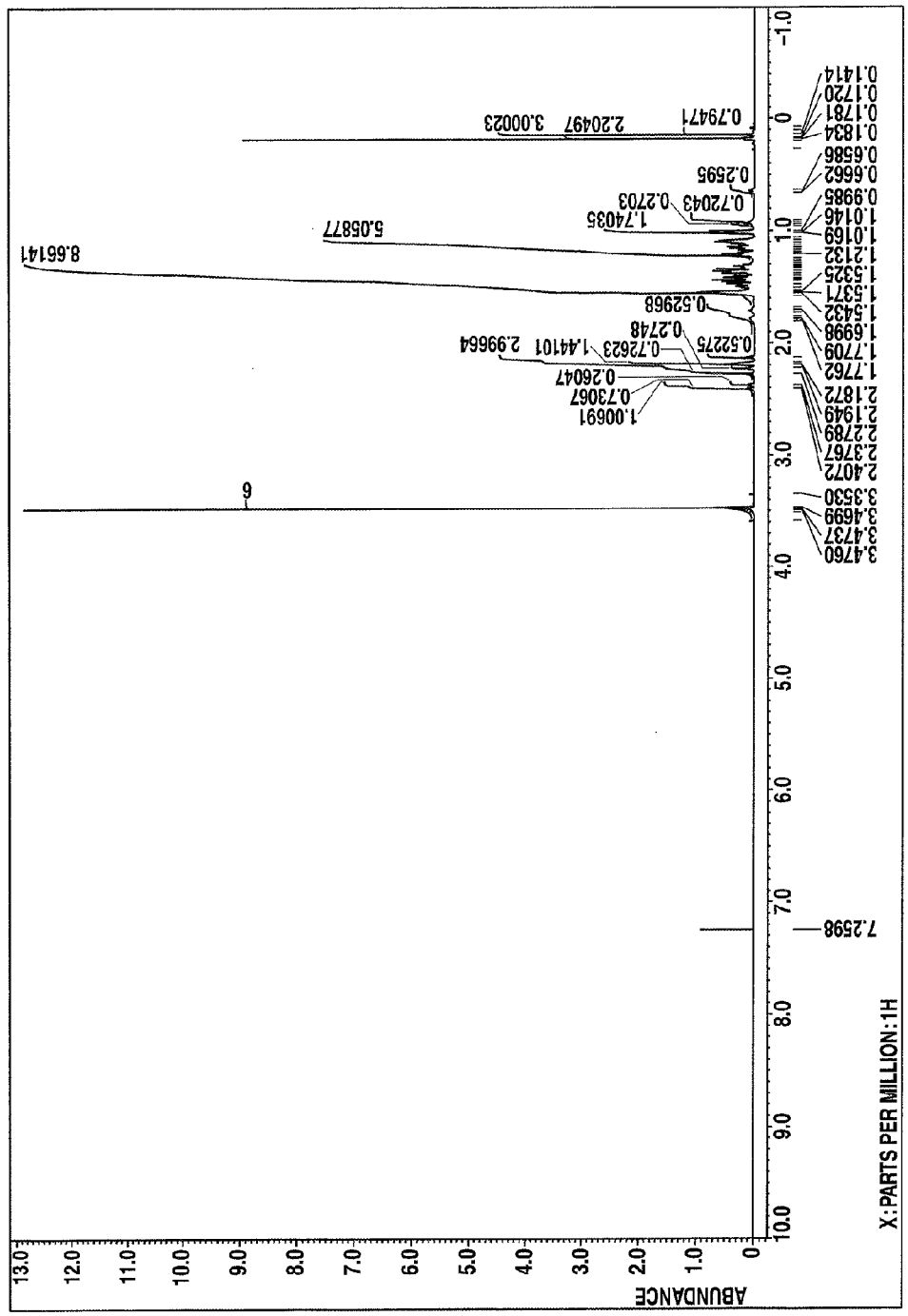

Mass Spectrum
m/z 294, 279, 262, 188, 105
$^1$H-NMR spectrum (deuterated chloroform): FIG. 7
IR Spectrum: FIG. 8

From these results, the compound was identified to be [3-(2-norbornyl)-2-norbornyl]methyldimethoxysilane.

Example 5

Preparation of
[3-(2-norbornyl)-2-norbornyl]trichlorosilane

A 200-ml four-neck glass flask equipped with a reflux condenser, thermometer and stirrer was purged with nitrogen and charged with 47.1 g (0.5 mole) of 2-norbornene in 15.7 g of toluene, and 11.2 mg (0.00005 mole) of palladium acetate. The contents were stirred for dissolution, after which 20.8 mg (0.0001 mole) of triisopropyl phosphite was added. The flask was heated at an internal temperature of 85° C., immediately after which dropwise addition of trichlorosilane was started. Specifically, 67.8 g (0.5 mole) of trichlorosilane was added dropwise over 4 hours while keeping the internal temperature at 85° C. to 95° C. The solution was ripened at the temperature for 1 hour.

On analysis of the resulting reaction solution by gas chromatography, the product ratio determined from peak areas of the desired [3-(2-norbornyl)-2-norbornyl]trichlorosilane:2-trichlorosilylnorbornane was 80.3:19.7.

Example 6

Preparation of
[3-(2-norbornyl)-2-norbornyl]trichlorosilane

A 300-ml four-neck glass flask equipped with a reflux condenser, thermometer and stirrer was purged with nitrogen and charged with 94.2 g (1.0 mole) of 2-norbornene in 31.4 g of toluene, and 22.5 mg (0.0001 mole) of palladium acetate. The contents were stirred for dissolution, after which 104.2 mg (0.0005 mole) of triisopropyl phosphite was added. The solution was stirred for 3 hours while keeping the internal temperature at 85° C. to 95° C. Thereafter, 81.3 g (0.6 mole) of trichlorosilane was added dropwise over 6 hours, followed by ripening at the temperature for 2 hours.

On analysis of the reaction solution by gas chromatography, the product ratio determined from peak areas of the desired [3-(2-norbornyl)-2-norbornyl]trichlorosilane:2-trichlorosilylnorbornane was 96.8:3.2. The reaction solution was distilled in vacuum, collecting [3-(2-norbornyl)-2-norbornyl]trichlorosilane as a fraction at a boiling point of 124-126° C./0.4 kPa. Amount 146.5 g (0.453 mole), yield 90.5%.

Japanese Patent Application No. 2012-235818 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A [3-(2-norbornyl)-2-norbornyl]silane compound having the general formula (1):

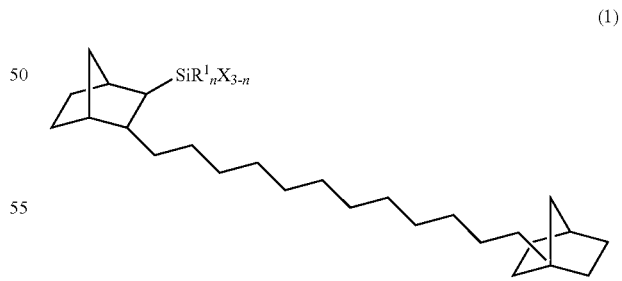

wherein $R^1$ is each independently a substituted or unsubstituted monovalent hydrocarbon radical of 1 to 10 carbon atoms, X is a halogen atom or an organoxy radical $OR^2$, $R^2$ is each independently a substituted or unsubstituted monovalent hydrocarbon radical of 1 to 10 carbon atoms, ∿∿∿∿∿ is a single bond, n is 1 or 2 when X is halogen, and n is 0, 1 or 2 when X is an organoxy radical.

2. A method for preparing a [3-(2-norbornyl)-2-norbornyl]halosilane compound having the general formula (3):

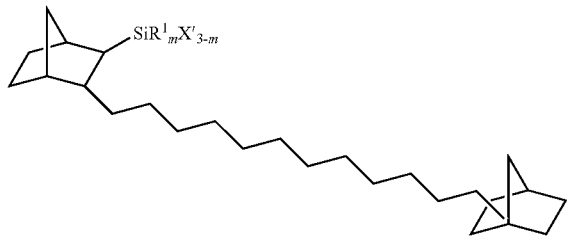
(3)

wherein $R^1$ is each independently a substituted or unsubstituted monovalent hydrocarbon radical of 1 to 10 carbon atoms, X' is a halogen atom, and m is 0, 1 or 2, the method comprising reacting a hydrosilane compound having the general formula (2):

$HSiR^1{}_mX'{}_{3-m}$ (2)

wherein R', X' and m are defined as above, with 2-norbornene in the presence of a phosphine-free palladium compound and a phosphite compound.

3. The method of claim 2 wherein the phosphite compound has the general formula (4):

$P(OR^3)(OR^4)(OR^5)$ (4)

wherein $R^3$, $R^4$ and $R^5$ are each independently a substituted or unsubstituted monovalent hydrocarbon radical of 1 to 10 carbon atoms.

4. The method of claim 2 wherein the palladium compound is palladium acetate.

5. The method of claim 2 wherein m is 1 or 2, and X' is chlorine.

6. A method for preparing a [3-(2-norbornyl)-2-norbornyl]-organoxysilane compound, comprising reacting a [3-(2-norbornyl)-2-norbornyl]halosilane compound obtained from the method of any one of claims 2 to 5 with an alcohol having the formula: R'OH wherein R' is a substituted or unsubstituted monovalent hydrocarbon radical of 1 to 10 carbon atoms.

* * * * *